(12) United States Patent
Ivri

(10) Patent No.: US 12,409,282 B2
(45) Date of Patent: *Sep. 9, 2025

(54) VIBRATION SYSTEMS AND METHODS

(71) Applicant: Stamford Devices Ltd, Galway (IE)

(72) Inventor: Yehuda Ivri, Newport Beach, CA (US)

(73) Assignee: Stamford Devices Ltd, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/807,085

(22) Filed: Jun. 15, 2022

(65) Prior Publication Data

US 2023/0108057 A1 Apr. 6, 2023

Related U.S. Application Data

(63) Continuation of application No. 16/570,177, filed on Sep. 13, 2019, now Pat. No. 11,389,603, which is a continuation of application No. 16/240,516, filed on Jan. 4, 2019, now abandoned, which is a continuation of application No. 14/816,975, filed on Aug. 3, 2015, now abandoned, which is a continuation of application No. 11/920,805, filed as application No.
(Continued)

(51) Int. Cl.
*A61M 15/00* (2006.01)
*B05B 17/00* (2006.01)
*B05B 17/04* (2006.01)

(52) U.S. Cl.
CPC ........ *A61M 15/0085* (2013.01); *A61M 15/00* (2013.01); *A61M 15/009* (2013.01); *B05B 17/04* (2013.01); *B05B 17/0646* (2013.01); *Y10T 29/42* (2015.01)

(58) Field of Classification Search
CPC .. A61M 11/005; A61M 15/00; A61M 15/001; A61M 15/0085; A61M 2205/0294; B05B 17/0607; B05B 17/0638; B05B 17/0646
See application file for complete search history.

(56) References Cited

U.S. PATENT DOCUMENTS 6,014,970 A * 1/2000 Ivri ..................... B05B 17/0684
128/200.14
6,530,370 B1 * 3/2003 Heinonen ......... A61M 15/0085
239/338

(Continued)

*Primary Examiner* — Joseph D. Boecker
(74) *Attorney, Agent, or Firm* — Bookoff McAndrews, PLLC

(57) ABSTRACT

In one arrangement, a vibration system includes a vibratable plate, a support member surrounding the vibratable plate, and a vibration-inducing member surrounding the support member. The vibration-inducing member is configured to radially expand and contract against the support member so as to produce axial vibration of the vibratable plate. In another arrangement, the vibratable plate has an outer circumference; a tubular member is concentrically disposed about the outer circumference of the plate, and an annular vibration-inducing member is concentrically disposed about the outer circumference of the tubular member. The vibration-inducing member is preferably a piezoelectric ring that is radially expandable and contractable against the wall of the tubular member to cause the plate to vibrate in the axial direction.

19 Claims, 11 Drawing Sheets

Related U.S. Application Data

PCT/US2006/014654 on Apr. 17, 2006, now Pat. No. 9,108,211.

(60) Provisional application No. 60/684,720, filed on May 25, 2005.

(56) References Cited

U.S. PATENT DOCUMENTS

| | | | |
|---|---|---|---|
| 6,769,626 B1* | 8/2004 | Haveri | A61M 15/0085 239/338 |
| 11,389,603 B2* | 7/2022 | Ivri | A61M 15/009 |
| 2002/0134372 A1* | 9/2002 | Loeffler | B05B 17/0646 128/200.14 |
| 2003/0047620 A1* | 3/2003 | Litherland | A61M 15/0085 239/102.1 |
| 2004/0050947 A1* | 3/2004 | Power | A61M 11/005 239/102.1 |

\* cited by examiner

VIBRATION SYSTEMS AND METHODS

CROSS-REFERENCE TO RELATED APPLICATIONS

This application is a continuation of U.S. patent application Ser. No. 16/570,177, filed on Sep. 13, 2019, which is a continuation of U.S. patent application Ser. No. 16/240,516, filed Jan. 4, 2019, which is a continuation of U.S. patent application Ser. No. 14/816,975, filed Aug. 3, 2015, which is a continuation of U.S. patent application Ser. No. 11/920,805, filed on Nov. 19, 2007, now U.S. Pat. No. 9,108,211, which is a 371 filing of PCT/US2006/014654, filed on Apr. 17, 2006, which claims the benefit of U.S. Provisional Application No. 60/684,720, filed on May 25, 2005, all of which are hereby incorporated by reference in their entirety.

BACKGROUND OF THE INVENTION

This invention relates generally to a vibration system that efficiently transfers radial vibration from a vibration-inducing member to produce axial vibration in a vibratable member through a support member that filters out undesirable vibration. In preferred embodiments, a piezoelectric transducer imparts ultrasonic oscillation to a vibratable plate, particularly a vibrating aperture (orifice) plate of an aerosol generator device, wherein the vibrating plate is perforated with holes and is operable in a fluid medium. The invention may also useful in the field of ultrasonic wave transmission in a fluid medium including, but not limited to, underwater sonar, depth sonar and obstacle detecting sonar.

Devices wherein a circular aperture plate is vibrated using a piezoelectric transducer in the form of a ring are well-known in the art. For example, in Maehara, U.S. Pat. No. 4,605,167, a vibratable plate having at least one nozzle opening therein is secured to a rigid housing and a piezoelectric ring is secured to the vibratable plate for inducing therein a displacement to discharge a small quantity of liquid through the nozzle opening. In other devices described in the art, a circular vibratable plate is directly bonded to the piezoelectric ring and covers the central opening in the piezoelectric ring; for example, as described in Toda, U.S. Pat. No. 5,297,734. As other examples, Humberstone et al., U.S. Pat. No. 5,518,179, Ross et al., U.S. Pat. No. 5,261,601 and Davison et al., U.S. Pat. No. 6,062,212 describe vibrating devices wherein a circular vibratable plate is mounted over the central opening of a thin annular member, or "washer", which is bonded to a piezoelectric ring. When actuated, the piezoelectric ring vibrates radially to cause the washer to operate in a "bending mode" that vibrates the vibratable plate in the axial direction. When these types of devices are manufactured the components must be carefully aligned concentrically with each other when the vibratable plate is attached to the washer and the washer is positioned over the opening in the piezoelectric ring.

Installing an ultrasonic transducer directly onto a rigid frame or housing, such as taught by Maehara, is also problematic. The reason is that the entire body of the transducer vibrates, with some portions vibrating at a small amplitude and some portions vibrating at an amplified amplitude. When the transducer is installed on the rigid fixture, the oscillation amplitude is reduced. Another problem with prior art arrangements is that the piezoelectric ring naturally vibrates in 3 directions (i.e., X, Y and Z axes) and transmits such vibration to the vibrating plate. The vibrations that are transmitted to the plate are superimposed and the contribution of the axial vibration may be canceled or partially canceled out. It is therefore desirable to filter out the undesirable vibration of the piezoelectric element and to use only vibration in a single direction, e.g., the axial direction. Attempts to address this problem have included mounting the vibratable plate on resilient retainer members, or "fingers", e.g., as described in Martens III et al., U.S. Pat. No. 6,450,419; supporting a bimorph-type transducer on rubber O-rings, e.g., as described in Ross et al., U.S. Pat. No. 5,261,601 and Humberstone et al., U.S. Pat. No. 5,518,179; and holding the piezoelectric ring in place with a grommet, e.g., as described in Helf et al., U.S. Pat. No. 6,293,474 and Tomkins et al., U.S. Pat. No. 6,382,522.

The above-described devices translate the radial vibration of a piezoelectric ring to axial vibration of a perforate plate to disperse a liquid as an aerosol. In another type of device, the piezoelectric transducer may be tubular and may expand and contract axially (in the direction of the central axis of the tube) to move a perforate plate. For example, see Newcombe et al., U.S. Pat. No. 5,838,350.

Generally, in a piezoelectric transducer that operates in a fluid medium, such as those used in aerosolizers, there is a need to separate the piezoelectric element from the vibratable element so that the vibratable element can be submerged in liquid and the piezoelectric element can be electrically insulated from the liquid. In some cases, such insulation may be provided by encasing the piezoelectric element with elastomer material. Such material, while providing electrical insulation, also has energy-absorbing characteristics that dampen the oscillation amplitude of the piezoelectric transducer and therefore has an adverse effect of the efficiency of the device.

There are currently a wide variety of aerosolizers and nebulizers. Of particular interest are those which vibrate an aperture plate or other element to produce the aerosol. Examples of some of these aerosolizers are described in U.S. Pat. Nos. 5,169,740, 5,938,117, 6,540,154, 5,586,550, 5,750,647, 6,467,476, 6,014,970, 6,755,189, 6,814,071, 6,554,201, 6,732,944, 6,615,824, 6,845,770, and 6,851,626, each of which is incorporated herein by reference in its entirety. One issue with aerosolizers (especially those used for medical applications using highly corrosive liquids) is contamination and corrosion of parts. Certain parts of the aerosolizer that are exposed to liquids may need to be washed or disposed of in order to keep the aerosolizer in good working order. Many of these parts are difficult to clean and, since piezoelectric transducers and their associated electronics can be relatively expensive, making them disposable may not be economically feasible. Therefore, it may be desirable to make certain aerosolizer components removable or replaceable.

BRIEF SUMMARY OF THE INVENTION

One or more embodiments of the present invention are directed to a vibration system that efficiently transfers radial vibration from a vibration-inducing member to produce axial vibration in a vibratable member through a support member that filters out undesirable vibration. In one particular arrangement, the vibration-inducing member may be an annular piezoelectric transducer having a central opening, the vibratable member may be a thin circular plate and the support member may have a circular cross-section for holding the circular plate; however, the components may also possibly have other shapes. In other arrangements, the vibration-inducing member is separable from the other structures so that it may be reused for other applications. In addition, other arrangements of the present invention effectively isolate the vibration-inducing member from contact with liquids and is therefore particularly adapted for operation in a fluid medium, e.g., in an aerosolizer environment. Still further, the present invention provides a method for self-aligning the components of a vibration system comprising a piezoelectric ring and a circular vibratable plate so as make manufacture of the system simple and inexpensive.

In one or more embodiments, the vibration system of the present invention comprises a thin circular vibratable plate, a tubular member holding the vibratable plate and a piezoelectric ring coupled to the tubular member. The vibratable plate may be concentrically disposed within the lumen of a thin-walled tubular member; and a piezoelectric ring may be concentrically positioned about the outer circumference of the tubular member at the location of the vibratable plate. The piezoelectric ring is expandable and contractable in the radial direction, which in turn causes the walls of the tubular member to expand and contract in the radial direction. This movement of the tubular member walls expands and contracts the outer circumference of the plate causing its middle region to oscillate (i.e., vibrate) in the axial direction. Since the outer circumference of the vibratable plate of the present invention is positioned within the central opening of the piezoelectric ring in alignment with its central plane, in contrast to prior systems wherein a surface of the vibratable plate (or concentric washer around the plate) is secured at the surface of the piezoelectric ring across the central opening of the piezoelectric ring, the radial load produced by the piezoelectric ring is more symmetrically applied to the vibratable plate of the present invention.

In one embodiment, the vibratable plate may be an aperture plate that includes a plurality of tapered apertures and is preferably dome-shaped. The aperture plate may be coupled to a mounting structure disposed within the lumen of the tubular member that holds the aperture plate perpendicular to the central axis of the tubular member.

In another embodiment, the tubular member may be fabricated from a corrosive-resistant metallic material, e.g., a palladium/nickel alloy or stainless steel, and have flexible thin walls, e.g., less than 0.5 mm in thickness. In other embodiments, the tubular member may comprise a plastic material, and may include at least one resilient segment, e.g., an elastomer, disposed therein that allows the tubular member to be compressed and expanded by the piezoelectric ring. In another embodiment, the piezoelectric ring may be removable from the tubular member and re-used for other applications. For example, the tubular member may be tapered to form a "taper lock" wherein the piezoelectric ring is press-fitted with the tubular member. In a still further embodiment, the piezoelectric ring may be permanently bonded to the tubular member to form an integral unit.

In one embodiment, a tubular member containing an aperture plate may be operably coupled to a reservoir of liquid, or the reservoir may be an integral part of the tubular member, so that liquid is supplied to the aperture plate within the tubular member. In this way, when the aperture plate is vibrated in accordance with the invention, liquid droplets are ejected from the aperture plate in the form of an aerosol. Optionally, a ring may be disposed about the outer periphery of the piezoelectric ring to assist in vibrating the aperture plate at its resonant frequency. In embodiments wherein the tubular member and the piezoelectric ring are not integrated with the reservoir, O-rings or other seals may be provided between the reservoir and the tubular member to serve as liquid-tight seals that prevent contamination of the piezoelectric ring, and also provide damping the piezoelectric ring and the aerosolizer housing, thereby increasing the efficiency of the system. In another embodiment, the tubular member may be "press-fitted" (i.e., form an "interference fit") with a discharge opening of the reservoir.

In one embodiment of the invention, the reservoir and the tubular member containing the aperture plate may be integrated as a single unit, and the piezoelectric ring may be slid over the reservoir of the aerosolizer to form a press-fit with the tubular member. In this way, the piezoelectric ring may be removed without potential contamination from substances within the reservoir or tubular member, or from aerosol produced by the aperture plate. In another embodiment, the piezoelectric ring and the tubular member may be bonded together as an integral unit.

The vibration system of the present invention may be incorporated into a variety of products and may be connected to power supplies, electronics to vibrate the vibration-inducing member, and the like. In one embodiment, the vibration system of the present invention is connected to a power supply using a first wire that makes electrical contact with a first surface of the piezoelectric ring and a second wire that makes electrical contact with a second surface of the vibration-inducing member. These wires may be located in grooves surrounding the outer surface of the housing in which the vibration system is located so that they are isolated from liquids in the reservoir and within the tubular member of the vibration system.

Examples of products that may employ the vibration system of the present invention include ventilators, continuous positive airway pressure (CPAP) systems, hand-held nebulizers and the like, as well as devices that utilize ultrasonic wave transmission in a fluid medium, such as, for example, various sonar devices. As one example, a ventilator circuit may comprise a length of tubing, and the vibration system of the present invention may be operably coupled to the tubing to introduce aerosol generated by the vibration system into the ventilator circuit. As another example, an aerosolizer may be constructed of a housing having a mouthpiece and the vibration system of the invention may be disposed in the housing so that liquid droplets produced by the vibrating aperture plate are ejected through the mouthpiece and into the respiratory system of the user.

One embodiment of the invention provides an exemplary method for making a vibration system comprising the steps of inserting a vibratable plate into a support structure that surrounds the plate; surrounding the support structure including vibratable plate with a vibration-inducing member that is configured to expand and contract radially; and actuating the vibration-inducing member to produce radial expansion and contraction against the support member to cause axial vibration of the vibratable plate.

In one particular embodiment, a method of making a vibration system comprises the steps of providing a tubular member with a lengthwise lumen, securing a circular vibratable plate within the lumen so that the vibratable plate is perpendicular to the central axis of the tubular member; providing a piezoelectric ring having a center opening; positioning the tubular member within the center opening of the piezoelectric ring so that outer circumference of the tubular member is in contact with the inner circumference of the opening and the vibration-inducing member surrounds the vibratable plate within the tubular member; and securing the vibration-inducing member to the tubular member.

In another embodiment, a method of vibrating a plate comprises the steps of inserting a vibratable plate in a support structure that surrounds the entire periphery of the plate, inserting the support structure including vibratable plate into the central opening of a vibration-inducing member that is configured to expand and contract radially, and actuating the vibration-inducing member to produce radial expansion and contraction against the support member that causes axial vibration of the vibratable plate.

In another embodiment, a method of treating a patient is provided, which comprises the steps of providing a vibration system comprising a circular vibratable aperture plate having an outer circumference, a tubular member concentrically disposed about the outer circumference of the vibratable plate, wherein the tubular member has an outer circumference, and an annular vibration-inducing member concentrically disposed about the outer circumference of the tubular member, wherein the vibration-inducing member is radially expandable and contractable to cause the aperture plate to vibrate in the axial direction; supplying a liquid medicament to the aperture plate via the tubular member; actuating the vibration-inducing member to vibrate the aperture plate and aerosolize the liquid medicament; and supplying the aerosol to a patient's respiratory system.

BRIEF DESCRIPTION OF THE DRAWINGS

FIG. 4b is a partial cross-sectional view of the aerosolizer shown in FIG. 4a.

FIG. 4c is a perspective view of the aerosolizer shown in FIG. 4a.

FIG. 7b is a cross-sectional side view of the aerosolizer of FIG. 7a.

DETAILED DESCRIPTION OF THE INVENTION

Figures 1A, 1B:
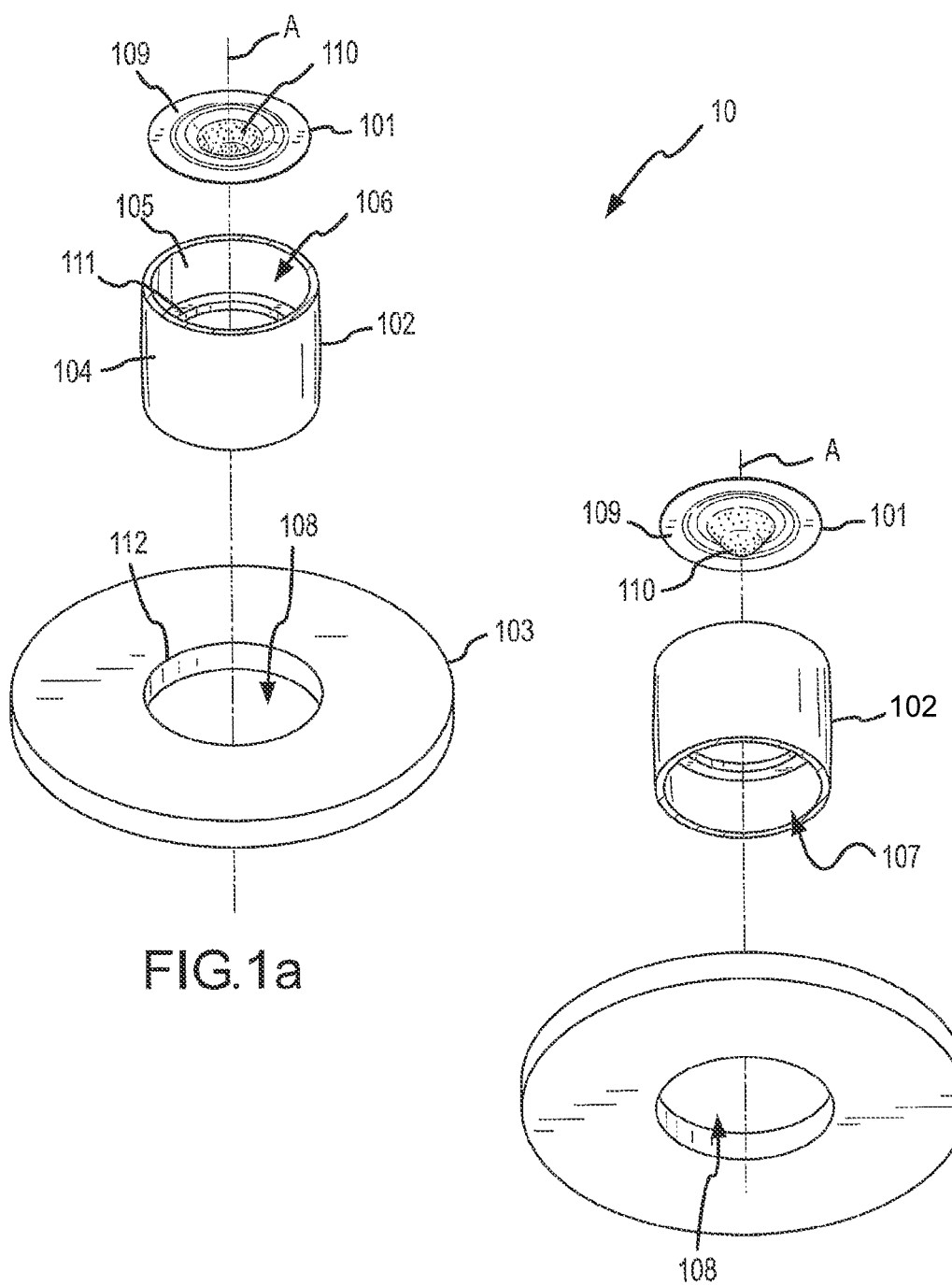
FIGS. 1a and 1b are exploded perspective views of a vibration system of the invention.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a", "an" and "the" include the plural unless the content clearly dictates otherwise.

Reference herein to "one embodiment", "one version" or "one aspect" shall include one or more such embodiments, versions or aspects, unless otherwise clear from the context.

In one or more embodiments, the vibration system of the present invention comprises a vibratable plate, a support member surrounding the vibratable plate, and a vibration-inducing member surrounding the support member, wherein the vibration-inducing member is configured to radially expand and contract the support member so as to produce axial vibration of the vibratable plate. The following detailed description is directed to one preferred embodiment of the invention wherein the vibratable plate is circular, the support member has a circular cross-section, e.g., a tubular member (cylindrical or tapered), into which the circular vibratable plate is disposed, and the vibration-inducing member is an annular disc having a central opening, i.e., a piezoelectric ring, into which the support member is disposed. However, it should be understood that the invention is not limited to this embodiment.

The tubular member may be manufactured from a corrosion-resistant metal, for example, stainless steel (preferably grades 316, 303 or 416), titanium, or a C-276 chrome/nickel alloy (e.g., Hastelloy® C-276). The tubular member preferably has relatively thin walls that can be effectively deflected by the piezoelectric ring. In one embodiment, the thickness of the walls of the tubular member is in the range of 0.1 mm to 0.5 mm, preferably about 0.25 mm. In one embodiment, the tubular member may have a shelf structure disposed around its inner surface to which the periphery of the vibratable plate may be bonded so that it extends across the internal lumen of the tubular member perpendicular to its central axis.

Various piezoelectric rings known in the art may be suitable for use as the annular vibration-inducing member of the present invention. In one embodiment, the piezoelectric ring may comprise any material exhibiting piezoelectric properties, for example, a piezoelectric ceramic material such as lead zirconate titanate (PZT) or lead metaniobate (PN) and may take the shape of a disc of substantially constant thickness with a central hole. Such piezoelectric rings are commercially available, e.g., from American Piezo Ceramics, Inc. (APC), Mackeyville, Pennsylvania, and from Morgan Electro Ceramics (MEC), Fairfield, New Jersey. The piezoelectric ring may be supplied with an alternating electric current at the selected frequency from a power source; for example, the piezoelectric ring may be electrically connected by wires to a controller that contains the electronics necessary to control the vibration of the piezoelectric ring.

In accordance with the invention, the tubular member is positioned within the center opening of the piezoelectric ring. When actuated by the alternating electrical fields from the controller, the piezoelectric ring expands and contracts in the radial direction against the walls of tubular member in the vicinity of the vibratable plate. This movement of the tubular member walls expands and contracts the periphery of the vibratable plate, thereby forcing the center of the vibratable plate to oscillate in the axial direction, i.e., to move up and down along the central axis of the tubular member. Although the piezoelectric ring may also vibrate in the axial direction and may create a transverse surface wave, only the radial vibration can transmitted to the vibratable plate by the tubular member. In this way, the superposition of conflicting vibration modes is eliminated and efficient translation of electrical energy to mechanical movement is accomplished. The practice of the present invention also allows the vibration system to be installed directly to a rigid body, such as the frame or housing of an aerosolizer, nebulizer or other device, without having the vibration transfer to the entire body. This is mainly because the ends of the tubular member do not vibrate and therefore may be used to install the vibration system to the rigid body.

The invention may be particularly useful when the tubular member is employed to hold an annular aperture plate or other structure having a plurality of apertures. When a liquid is applied to one side of the aperture plate through the tubular member and the piezoelectric ring is actuated, the aperture plate oscillates in a manner that causes liquid droplets to be ejected from the apertures. The resultant aerosol may then be dispensed out the open end of the tubular member.

A particularly useful type of aperture plate is one having tapered apertures that taper from the surface contacting the liquid to the surface where the droplets are ejected. Also, in some embodiments, the aperture plate may be domed shaped, although the invention is not limited to only such aperture plates. Preferred aperture plates may have a thickness in the range of 20 to 100 microns. Examples of piezoelectric materials and aperture plates that may be used with the invention are described in U.S. Pat. Nos. 6,235,177 and 5,758,637, incorporated herein by reference. In another embodiment, the piezoelectric ring may be vibrated at a frequency in the range from about 20 Khz to about 500 Khz, for example, about 128 Khz. In another preferred embodiment, the droplets may have a size suitable for use in pharmaceutics, for example, in the range from about 3 micrometers (μm) to about 6 μm, and the liquid may be aerosolized at a rate in the range from about 5-20 microliters/second.

Figure 2:
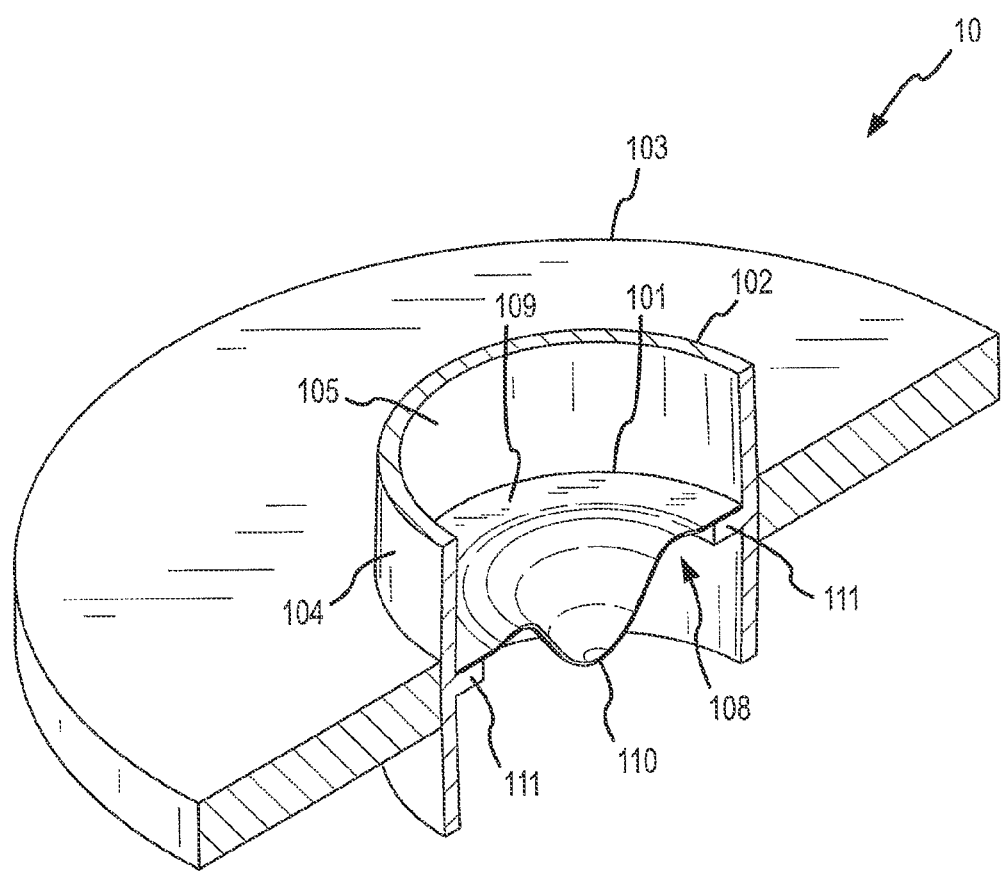
FIG. 2 is a partial cross-sectional view of the assembled vibration system of FIGS. 1a and 1b.

Referring now to FIGS. 1a, 1b and 2, one embodiment of the present invention will be described. Vibration system 10 comprises vibratable plate 101, tubular member 102 and piezoelectric ring 103. Tubular member 102 has an outer circumference 104 and an inner circumference 105, which together define a relatively thin cylindrical wall, preferably having a thickness in the range from about 0.1 mm to 0.5 mm. The hollow center (lumen) of tubular member 102 terminates in openings 106 and 107 at opposing ends thereof. Mounting structure 111 comprises a circular ridge that projects perpendicularly from inner circumference 105 into the lumen of tubular member 102 at a location, preferably a central location, between openings 106 and 107. Piezoelectric ring 103 comprises an annular disc of piezoelectric material having a center hole 108 with a circumference 112 approximately equal to the outer circumference 104 of tubular member 102. Vibratable plate 101 comprises circular outer flange 109 surrounding a thin circular vibratable center portion 110.

In one method of making vibration system 10, metallic tubular member 102 may first be provided with mounting structure 111 by bonding a ridge of metal around inner circumference 105 at a location equidistant from ends 106 and 107. Vibratable plate 101 may then be concentrically disposed within the lumen of tubular member 102 with the lower surface of circular flange 109 positioned over the upper surface of mounting structure 111 and with the outer periphery of vibratable plate 101 abutting inner circumference 105. Outer flange 109 of vibratable plate 101 may be secured onto mounting structure 111 using a suitable joining procedure, e.g., a metallurgical process such as brazing, welding, soldering or the like, or a chemical bonding process such as adhesive bonding.

In one preferred embodiment, a brazing ring of a suitable corrosion-resistant brazing filler material, e.g., a mixture of 70% gold and 30% copper, may be placed between the upper surface of mounting structure 111 and outer flange 109 of vibratable plate 101. The entire assembly of tubular member 102, vibratable plate 101 and brazing ring may be held in place by a weight placed on top of vibratable plate 101. The assembly may be placed in an oven and heated to a temperature sufficient to melt the brazing 1 and permanently join the surfaces together in a conventional brazing procedure. In another embodiment, vibratable plate 101 may be soldered onto mounting structure 111 using soldering materials, such as a tin/lead soldering material; however, this method may not be suitable if the assembly is to be exposed to acidic pharmaceutical preparations. In another embodiment, vibratable plate 101 may be secured onto mounting structure 111 by ultrasonic or laser welding.

Once vibratable plate 101 is secured across the lumen of tubular member 102, tubular member 102 may be positioned within center hole 108 of piezoelectric ring 103. In one embodiment, tubular member 102 may be placed in a fixture that holds tubular member 102 upright, and piezoelectric ring 103 may be slid lengthwise down tubular member 102 until piezoelectric ring 103 surrounds the outer circumference 104 at a location directly corresponding to the location of mounting structure 111 and vibratable plate 101 on inner circumference 105 of tubular member 102. Outer circumference 104 of tubular member 102 and circumference 112 of center hole 108 in piezoelectric ring 103 may then be bonded together, e.g., by depositing a suitable liquid adhesive around the juncture of circumference 104 and circumference 112 and curing the adhesive, e.g., with UV light. The adhesive used should be capable of efficiently transferring vibration from the piezoelectric ring 103 to tubular member 102. Although ideally the adhesive would have the modulus of elasticity ("Young's Modulus") of the piezoelectric ring, i.e., about 60 GPa (Giga Pascal), to achieve the ultimate transfer of vibration, this is not possible for any adhesive. Most structural adhesives (such as epoxy) have a modulus of elasticity of plastic material, which may be about 2 GPa, and should be suitable for the present invention if cured to approximately that stiffness. As examples of suitable adhesives, mention may be made of various epoxy and anaerobic adhesives, such as commercially available UV-cured epoxy adhesives sold under the trademark Loctite.

Figure 3A:
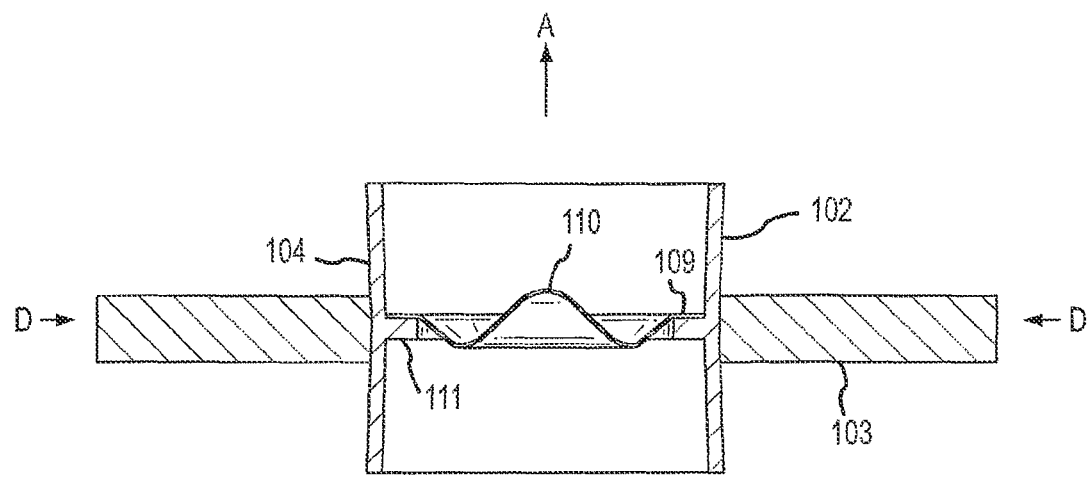
FIGS. 3a and 3b are cross-sectional side views of the vibration system of FIG. 2.
Figure 3B:
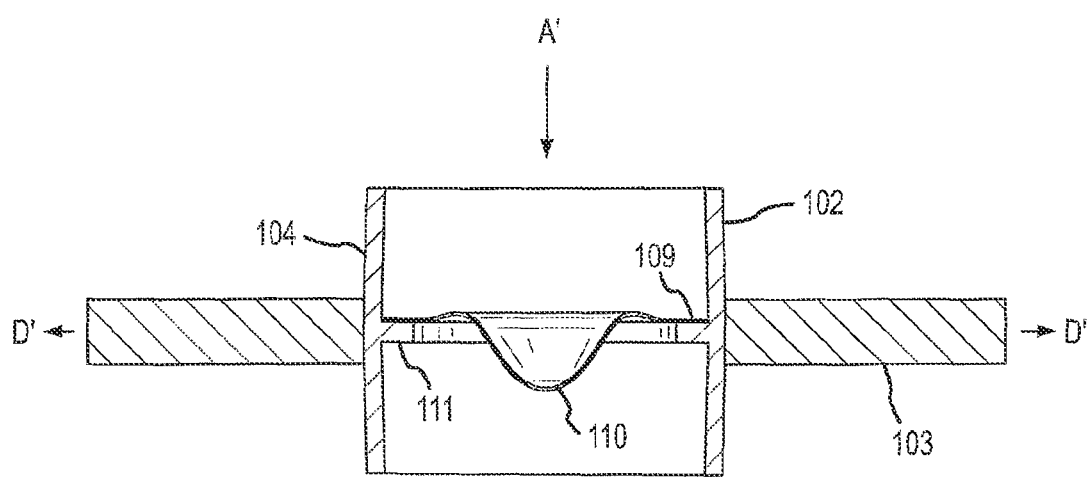

As previously described, piezoelectric ring 103 is configured to radially expand and contract when alternating electric fields are communicated to it via electric lines. For example, as illustrated in FIG. 3a, piezoelectric ring 103 contracts radially towards its center opening (direction D) when actuated by a first electric field. This radial contraction causes piezoelectric ring 103 to push inward along outer circumference 104 of tubular member 102 in the vicinity of mounting structure 111 and thereby pinch the wall of tubular member 102. The constriction of tubular member 102 causes flange 109 to also constrict radially and, as a result, the center portion 110 of vibratable plate 101 moves axially in direction A. When actuated by a second electric field, as shown in FIG. 3b, piezoelectric ring 103 expands radially away from its center opening (direction D'), thereby releasing the inward pressure along circumference 104 of tubular member 102. This release of pressure allows flange 109 to expand radially, which causes center portion 110 of aperture plate 101 to move axially in direction A' to its original position. Continually alternating the electric fields produces an oscillation (vibration) of center portion 110 between the positions shown in FIGS. 3a and 3b.

Figure 4A:
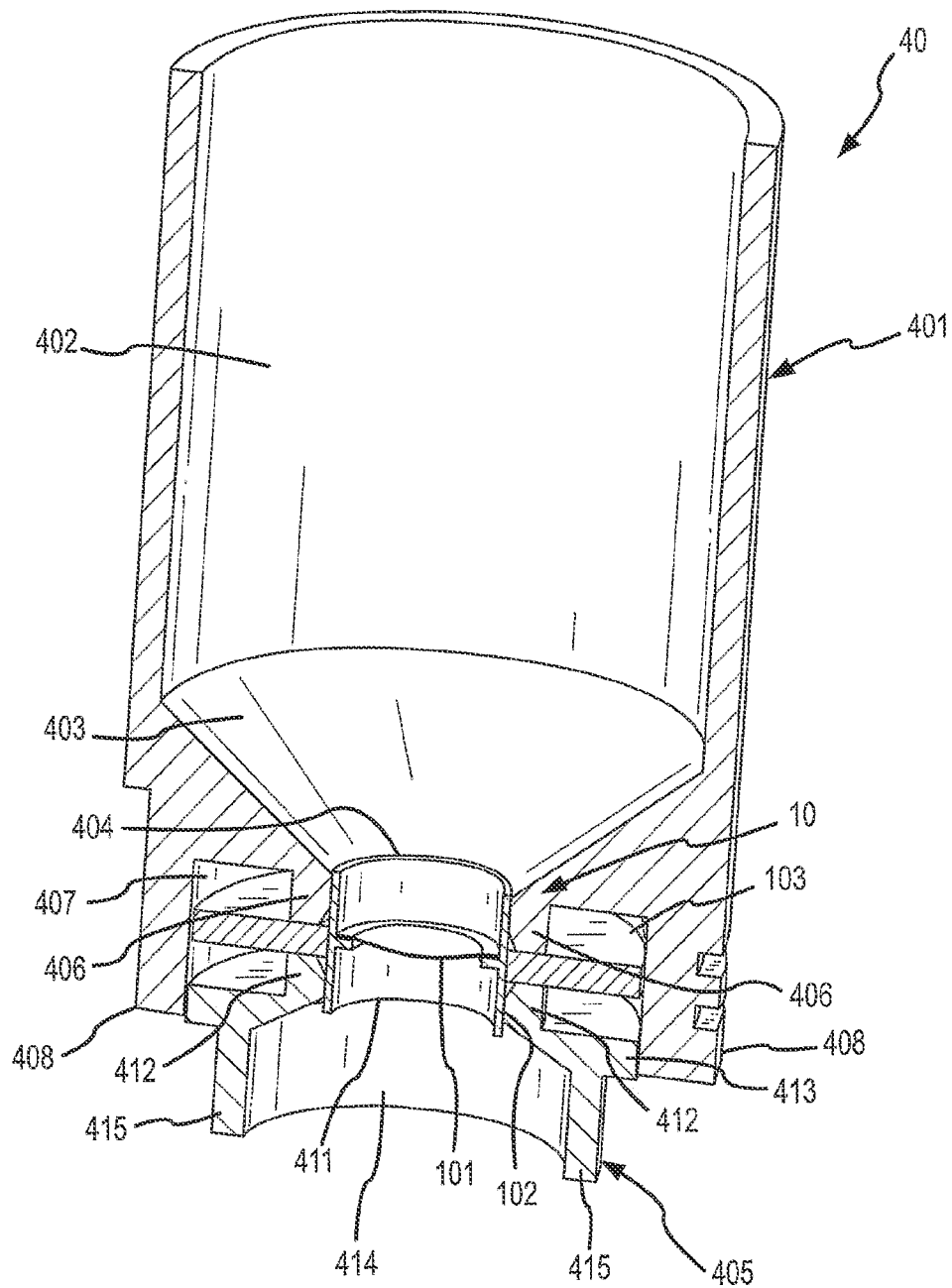
FIG. 4a is a cross-sectional side view of one embodiment of an aerosolizer according to the invention.
Figure 4B:
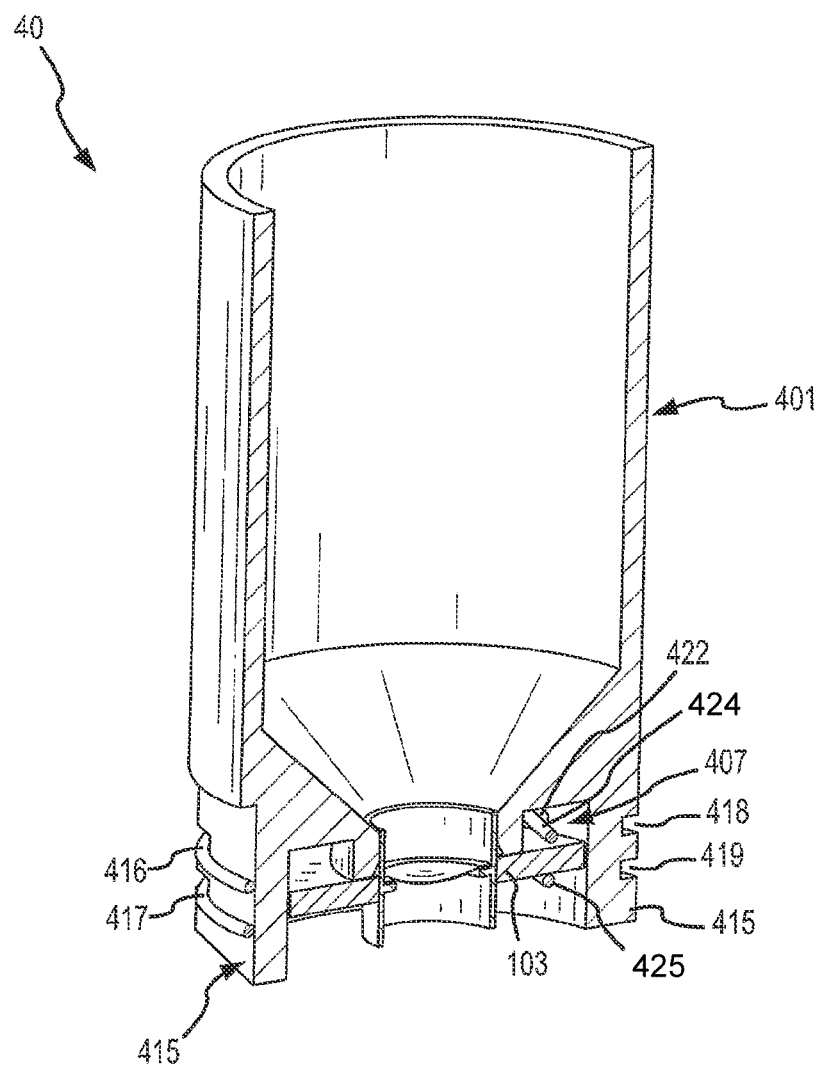
Figure 4C:
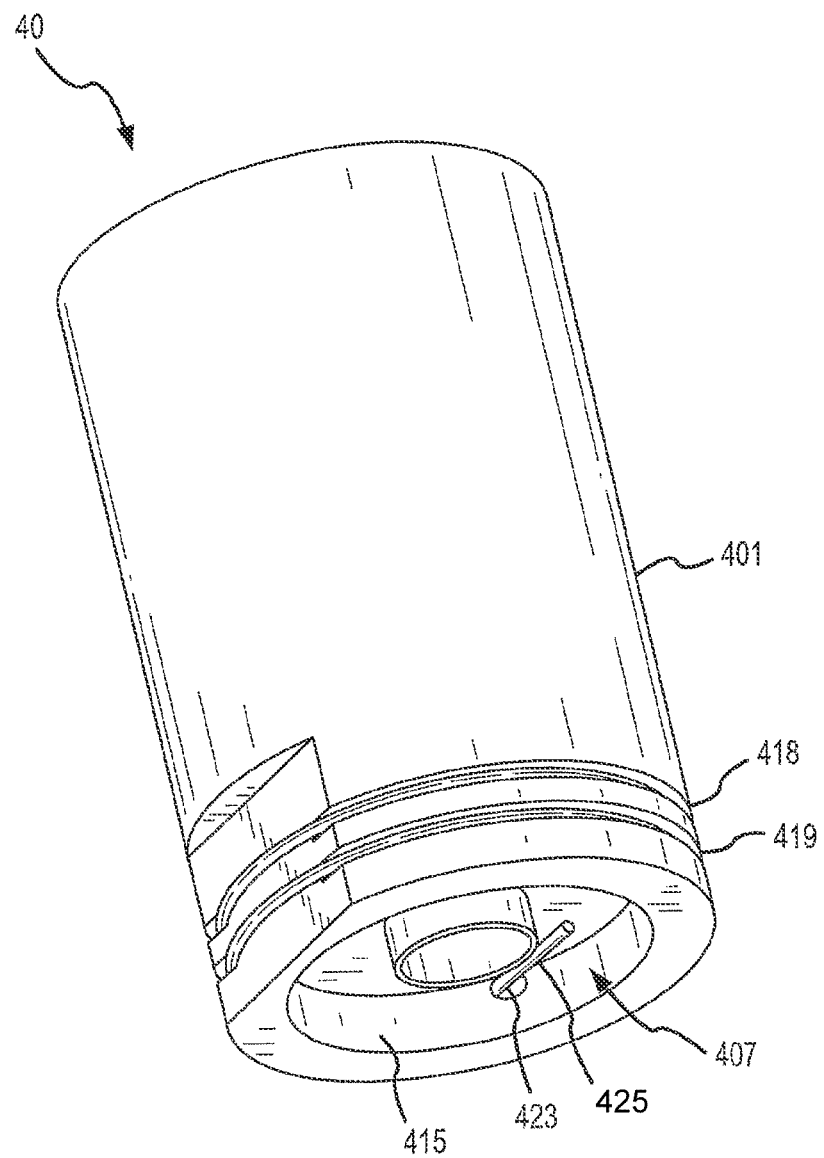
Figure 4D:
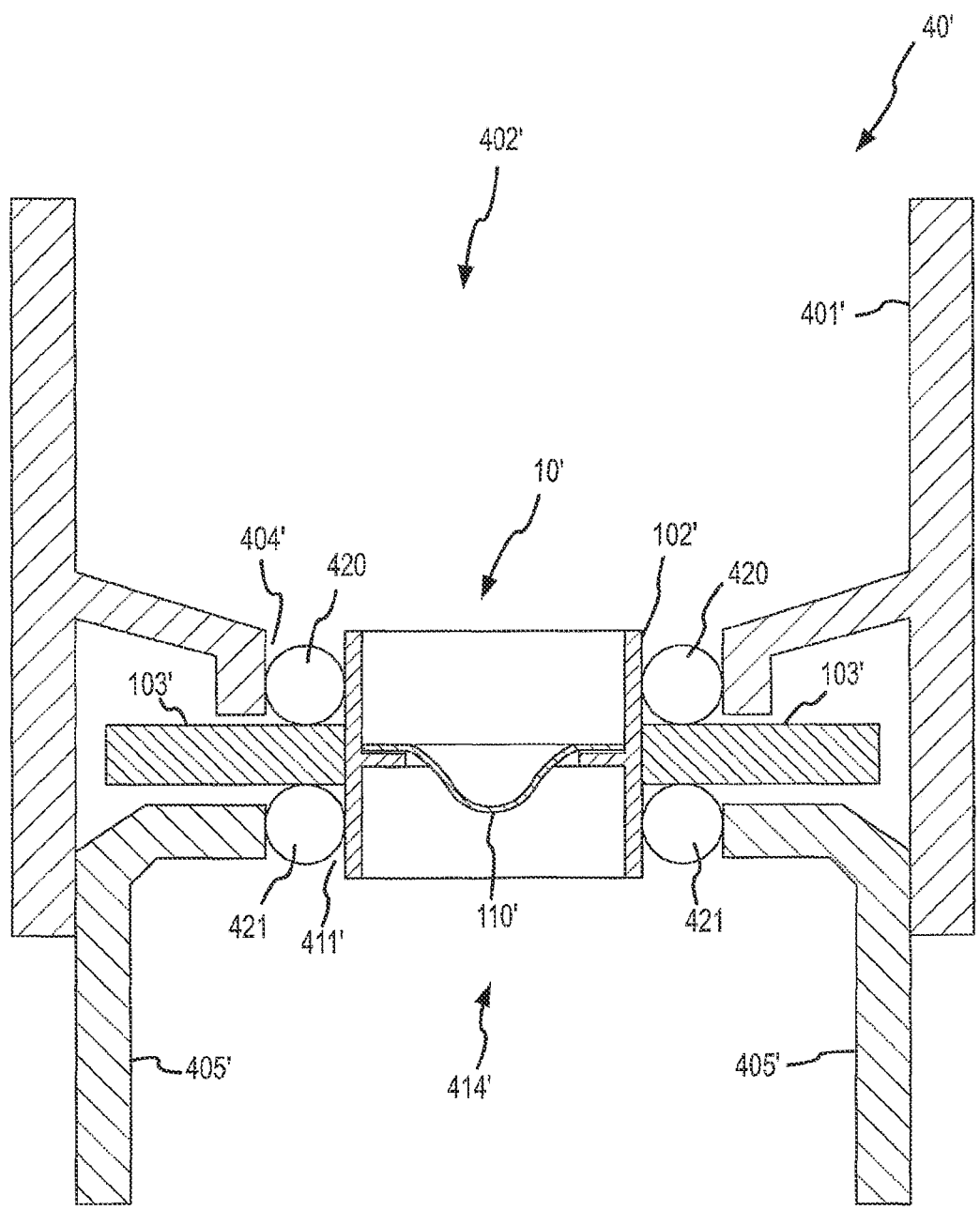
FIG. 4d is a cross-sectional side view of another embodiment of an aerosolizer according to the invention.

As previously mentioned, the vibration system of the present invention is particularly useful for aerosolizing liquids. FIGS. 4a, 4b and 4c illustrate an aerosolization system (referred to herein as "aerosolizer 40") in accordance with embodiments of the present invention. The same reference numbers are used in each of the Figures to refer to the same component. Referring now to FIG. 4a, aerosolizer 40 comprises upper housing 401, detachable lower housing 405 and vibration system 10 (e.g., see FIG. 2). Vibration system 10 comprises tubular member 102, piezoelectric ring 103 and aperture plate 101. Upper housing 401 comprises reservoir 402 configured to hold a volume of liquid, e.g., a liquid medicament, and a conical portion 403 at the lower end of reservoir 402 terminating in discharge tube 404 defined by cylindrical walls 406. Engagement tube 407 defined by cylindrical walls 408 of upper housing 401 is concentrically disposed around and completely encompasses discharge tube 404.

Vibration system 10 is adapted to be detachably engaged with upper housing 401, with the upper section of tubular member 102 of vibration system 10 (i.e., that section of tubular member 102 above piezoelectric ring 103) being configured to be press fit within discharge tube 404 and with piezoelectric ring 103 of vibration system 10 being configured to be press fit with engagement tube 407. When assembled, the upper section of tubular member 102 of piezoelectric ring 103 is fully encompassed by discharge tube 404 and the top surface of piezoelectric ring 103 abuts the lower end of discharge tube 404. This press fit mating of tubular member 102 and discharge tube 404 forms a liquid-tight seal that prevents liquid discharged from reservoir 402 into discharge tube 404 from coming in contact with piezoelectric ring 103.

Lower housing 405 comprises receiving tube 411 defined by cylindrical walls 412, annular flange 413 concentrically disposed around the base of receiving tube 411 and aerosol chamber 414 defined by cylindrical walls 415. Lower housing 405 may be adapted to be detachably engaged with vibration system 10 and upper housing 401, with the lower section of tubular member 102 of vibration system 10 (i.e., that section of tubular member 102 below piezoelectric ring 103) being configured to be press fit within receiving tube 411 and with annular flange 413 being configured to be press fit within engagement tube 407. When assembled, the lower section of tubular member 102 is fully encompassed by receiving tube 411 and forms a passageway directly into aerosol chamber 414. The bottom surface of piezoelectric ring 103 abuts the upper end of receiving tube 411 to securely hold vibration system 10 within engagement tube 407.

Referring now to FIGS. 4*b* and 4*c*, piezoelectric ring 103 may be supplied with an electric current by wires 416 and 417 from batteries or another power source (not shown). Each of wires 416 and 417 may be shaped in a "c-clip" arrangement and respectively nestled into grooves 418 and 419 cut around the periphery of walls 415 of upper housing 401. Terminal end 424 of wire 416 may enter engagement tube 407 through opening 422 in wall 415 and make electrical contact with the upper surface of piezoelectric ring 103. Terminal end 425 of wire 417 may enter engagement tube 407 through hole 423 in wall 415 of upper housing 401 and make electrical contact with the lower surface of piezoelectric ring 103.

Center portion 110 of aperture plate 101 may be dome-shaped in geometry, although other shapes may be used. Also, center portion 110 may include apertures that taper from the rear side (facing reservoir 402) to the front side. When aerosolizer 40 is placed in a generally vertical orientation, the liquid from reservoir 402 may be delivered to and rest on the rear side of center portion 110 by force of gravity. Piezoelectric ring 103 is configured to radially expand and contract when actuated by alternating electric fields supplied by wires 416 and 417. In so doing, the wall of tubular member 102 also constricts and expands. In this way, center portion 110 vibrates axially so as to eject liquid droplets from its front side and out the opening in aerosol chamber 414.

One advantage of using vibration system 10 is that aerosolizer 40 may be constructed so that vibration system 10 is removable from upper housing 401 and lower housing 405. In this way, vibration system 10 (which contains relatively expensive piezoelectric ring 103) may be reused in other applications. Upper housing 401 and lower housing 405, which may be able to be produced relatively inexpensively, may be discarded after use. Another advantage of using vibration system 10 is that the ends of tubular member 102 may be connected directly to rigid bodies, such as wall 406 of upper housing 401 and wall 412 of lower housing 405, without affecting the oscillating amplitude of aperture plate 110. This enables aerosolizer 40 to more efficiently produce liquid droplets.

Referring now to FIG. 4*d*, aerosolizer 40' is similar to aerosolizer 40 and comprises upper housing 401' containing reservoir 402', detachable lower housing 405' containing aerosol chamber 414', and vibration system 10', which comprises tubular member 102', piezoelectric ring 103' and aperture plate center portion 110'. However, in aerosolizer 40', the upper section of tubular member 102' is not press fit into discharge tube 404' (as shown in FIG. 4*a*), but rather O-rings 420 may be positioned to fill a gap between the upper section of tubular member 102' and discharge tube 404' of housing 401'. In this way, a liquid-tight seal is formed that prevents liquid from reservoir 402' from contacting piezoelectric ring 103'. Similarly, O-rings 421 may be positioned to fill a gap between the lower section of tubular member 102' and receiving tube 411' of lower housing 405' to form a liquid-tight seal that prevents aerosol produced from aperture plate center portion 110' from contacting piezoelectric ring 103'. Accordingly, piezoelectric ring 103' may be protected from contamination that may prevent it from being reusable after removal from aerosolizer 40', without the tight dimensions required for a press fit, as described in connection with aerosolizer 40. Since O-rings 420 and 421 are positioned on both top and bottom surfaces of piezoelectric ring 103' and serve to suspend piezoelectric ring 103' from direct contact with upper housing 401' and lower housing 405', O-rings 420 and 421 may also have a dampening effect that reduces the undesirable transfer of vibration from piezoelectric ring 103' to upper housing 401' and lower housing 405'.

Referring now to FIGS. 5*a* and 5*b*, another embodiment of the present invention will be described. Vibration system 50 comprises a piezoelectric ring 502 having a central opening 504. Piezoelectric ring 502 may be constructed of a piezoelectric material that radially expands and contracts when actuated, as previously discussed. Tubular member 506 is disposed within opening 504 and is adapted to hold aperture plate 508 within its internal lumen 509 using any of the techniques described herein. Tubular member 506 may be constructed of a rigid material, such as a hard plastic, metal, ceramic or the like. Tubular member 506 may optionally include projections 510 to provide a good mechanical contact with piezoelectric ring 502. As an alternative, tubular member 506 may be tapered to assure a good mechanical contact.

Tubular member 506 may include one or more resilient segments 511 radially extending from locations on its inner circumference to corresponding locations on its outer circumference. These segments may be constructed from an elastomeric material and positioned in various locations. Resilient segments 511 permit tubular member 506 to be constructed of a rigid material (for securely holding aperture plate 508) while also permitting tubular member 506 to radially expand and contract with piezoelectric ring 502. More specifically, as tubular member 506 is constricted by piezoelectric ring 502, resilient segments 511 compress to reduce the diameter of lumen 509. When piezoelectric ring 502 radially expands, resilient segments 511 expand to increase the diameter of lumen 509. Hence, the amount of expansion and contraction may be varied based in part on the size, number and types of resilient materials used.

Conveniently, vibration system 50 may be coupled to a reservoir of an aerosolizer (not shown) to permit a liquid to be supplied to aperture plate 508. Also, other liquid delivery systems could be used as well, such as wicking systems, and the like. Alternatively, vibration system 50 may be incorporated into other systems, such as nebulizers, ventilators and the like.

Figure 5A:
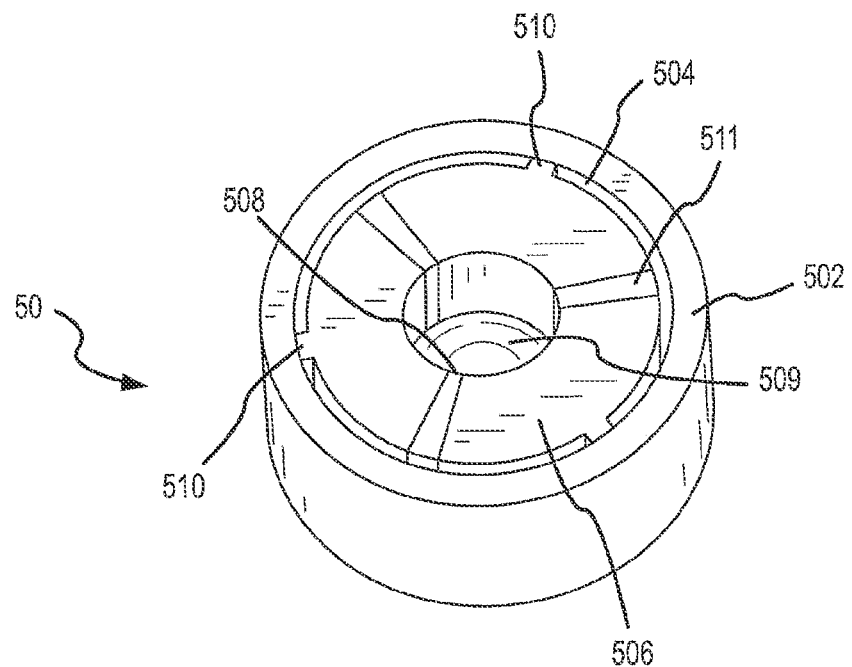
FIG. 5a is a perspective view of another embodiment of a vibration system according to the invention.
Figure 5B:
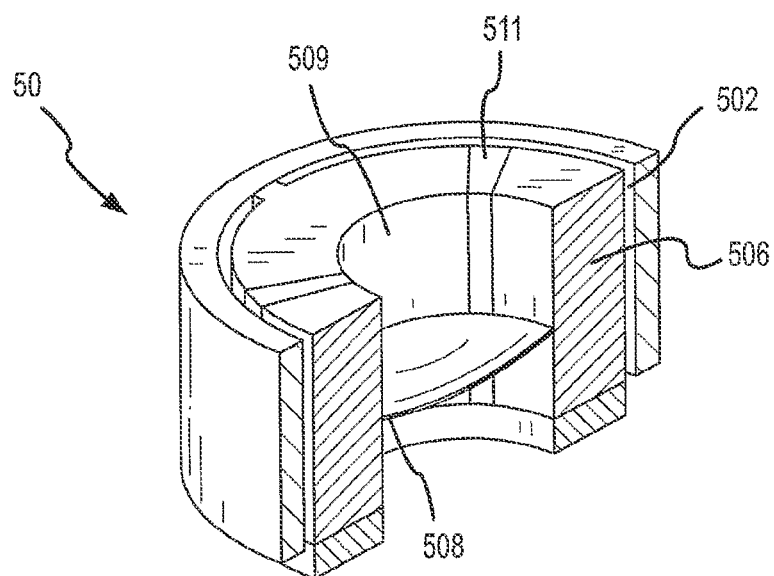
FIG. 5b is a partial cross-sectional view of the vibration system shown in FIG. 5a FIG. 6 is a perspective view of another embodiment of a vibration system according to the invention.
Figure 6:
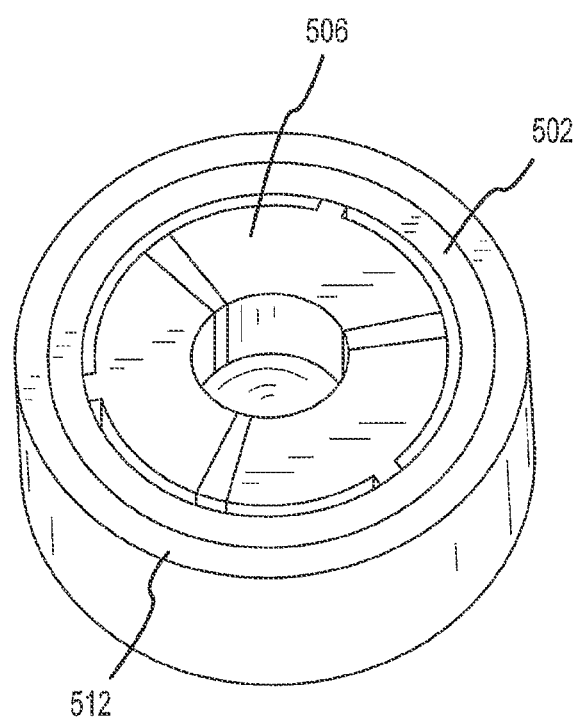

FIG. 6 illustrates vibration system 50, as shown in FIGS. 5a and 5b, with an outer ring 512 disposed about the outer circumference of piezoelectric ring 502, which in turn in disposed around tubular member 506. Ring 512 may be employed to adjust the operating frequency of piezoelectric ring 502. In many applications, it is desirable to operate piezoelectric ring 502 at a frequency of about 130 Khz, which is the approximate resonance frequency of the aperture plate. When piezoelectric ring 502 is constructed from a piezoceramic material, its frequency is inversely proportional to its diameter where:

$$f = (1/2\pi i r) \times \sqrt{(E/p)}$$

Hence, if the diameter of the piezoelectric ring 502 is made larger to reduce the frequency of the piezoelectric ring, the piezoelectric ring 502 may be too large for certain applications. A low operating frequency of piezoelectric ring 502 may result because the piezoelectric material is "soft" and heavy. To increase the frequency without increasing the diameter, outer ring 512 (which may be constructed of a stiff and lightweight material, such as silicon nitride) may be added. The combination of ring 512 and piezoelectric ring 502 serves to increase the frequency to the desired range.

Figure 7A:
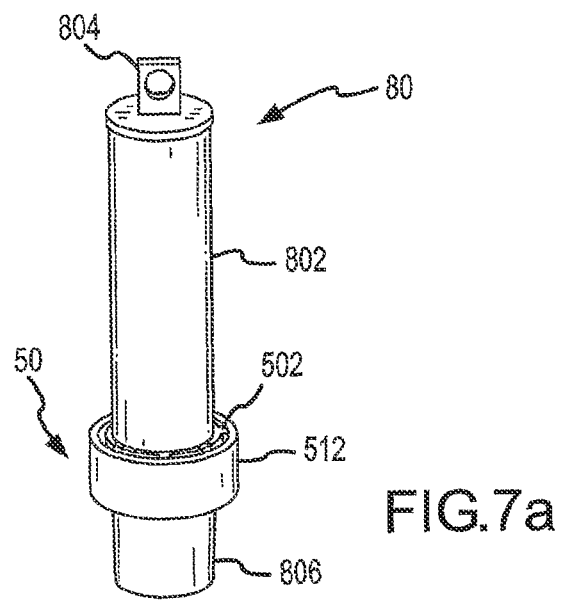
FIG. 7a is a perspective view of another embodiment of an aerosolizer according to the invention.
Figure 7B:
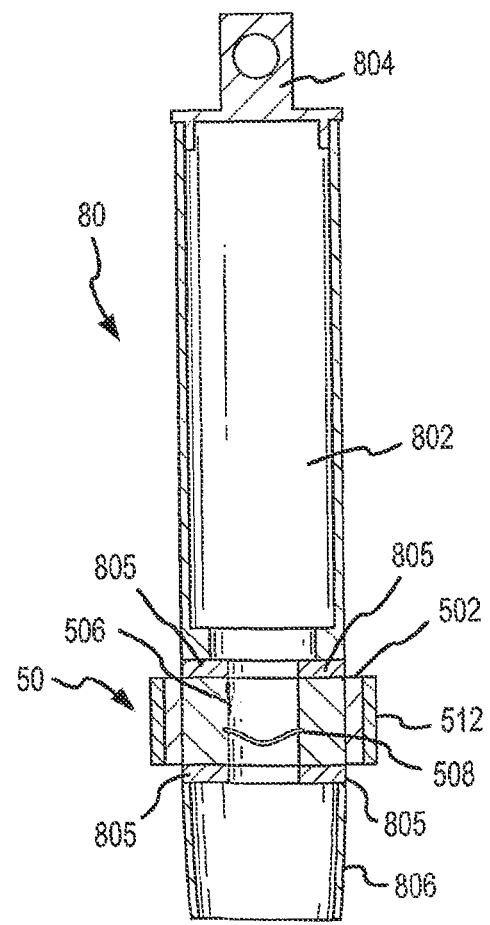

Referring to FIGS. 7a and 7b, an embodiment of an aerosolization system in accordance with the present invention will be described. System 80 includes an aerosolizer that, for convenience of discussion, includes vibration system 50 having ring 512, as shown in FIG. 6, although it will be appreciated that other vibration systems of the invention could be used as well. Coupled to (or integrally formed with) tubular member 506 of vibration system 50 is a container 802 for holding a liquid. Conveniently, a lid 804 may be provided to close container 802 after filling it with a liquid. Also coupled to tubular member 506 is an outlet 806 through which an aerosol produced by aperture plate 508 may be dispensed. O-rings or gasket seals 805 may be disposed between container 802 and vibration system 50, and between vibration system 50 and outlet 806 to provide adequate sealing and cushioning between the components.

One particular feature of aerosolization system 80 is that piezoelectric ring 502 has a large enough inner diameter that it may be slid over outlet 806 and container 802. In this way, system 80 may be easily assembled and disassembled to remove piezoelectric ring 502. Further, piezoelectric ring 502 does not come into contact with any liquids and therefore may be reused with another aerosolization system. Further, container 802, tubular member 506 and aperture plate 508 may be constructed to be relatively inexpensive so that they may be disposed of following use. Also, system 80 may easily be incorporated into other systems, such as hand-held nebulizers, ventilators and the like.

In operation, container 802 is filled with a liquid and lid 804 is put in place. Piezoelectric ring 502 is slid over container 802 and placed over tubular member 506. An electric current is supplied to piezoelectric ring 502 to cause it to expand and contract. In so doing, liquid that is in contact with aperture plate 508 is ejected as liquid droplets into outlet 806. Following use, container 802 may be refilled, or may be discarded while saving piezoelectric ring 502.

Figure 8:
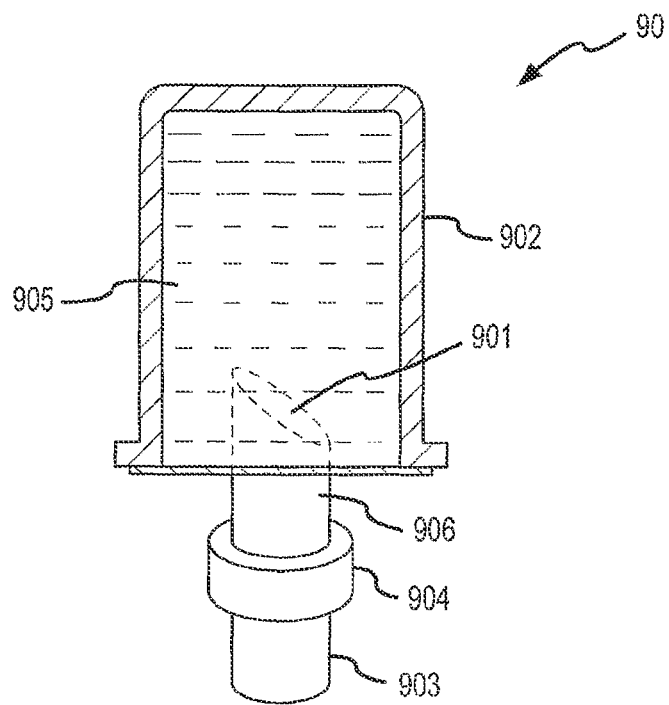
FIG. 8 is a cross-sectional side view of another embodiment of an aerosolizer system according to the invention.

FIG. 8 illustrates another embodiment of the invention wherein aerosolization system 90 includes tubular member 906 comprising a sharpened end 901 and a discharge end 903. As previously described, tubular member 906 also contains an aperture plate (not shown) across its internal lumen. Piezoelectric ring 904 is disposed around tubular member 906. When aerosolization system 90 is not in use, sharpened end 901 may have a cover (not shown) that protects it from damage and contamination. When ready for use, the cover may be removed and sharpened end 901 may be inserted through the membrane top of a vial 902, which contains liquid 905 to be aerosolized. Liquid 905 is then delivered through sharpened end 901 and the lumen of tubular member 906 to the aperture plate contained therein. Piezoelectric ring 904 may be actuated to vibrate the aperture plate and thereby aerosolize liquid 905 in the manner previously described. The resultant aerosol is then dispensed through discharge end 903. After use, vial 902 may be removed from sharpened end 901 and discarded, piezoelectric ring 904 may be removed from the assembly for re-use, and the remaining assembly may be discarded.

As previously mentioned, the aerosolizers described herein may be incorporated into other systems. Example of ventilator systems are described, for example, in co-pending U.S. patent application Ser. No. 10/828,765, filed Apr. 20, 2004, the complete disclosure of which is herein incorporated by reference. The system described therein is particularly useful in neo-natal and infant continuous positive pressure airway pressure (CPAP) therapies. Accordingly, an aerosolizer of the present invention may be coupled to such a ventilator or CPAP circuit to supply aerosolized medicament to a patient's respiratory system, e.g., through a patient interface device. When the treatment is finished, the aerosolizer, or certain components thereof, may be removed and re-used, while other components of the system may be discarded.

As another example, the aerosolizer of the present invention may be incorporated in a nebulizer such as described in co-pending U.S. patent application Ser. No. 10/833,932, filed Apr. 27, 2004, the complete disclosure of which is herein incorporated by reference. The nebulizer comprises a main housing coupled to an aerosolizer housing, which may comprise an aerosolization system such as previously described in connection with aerosolizer 40 shown in FIGS. 4a, 4b and 4c, including a reservoir for holding a liquid medicament that is to be aerosolized and a vibration system according to the present invention having an aperture plate with a plurality of tapered apertures extending between a first surface and a second surface, as described in U.S. Pat. Nos. 5,164,740, 5,586,550, 5,758,637, and 6,085,740, the entire contents of which are incorporated herein by this reference. The nebulizer may also have a mouthpiece coupled to the main housing. At least a portion of the tubular member of the vibration system of the present invention may be disposed in the housing so that liquid droplets are ejected through the mouthpiece to permit a patient to inhale the aerosolized medicament. The apertures in the aperture plate may be sized to produce an aerosol in which about 70% or more of the droplets by weight have a size in the range from about 1 to about 5 micrometers. Following use, the aerosol housing may be removed from the main housing. The liquid may be refilled, or one or more components may be replaced. For example, the vibration system may be removed and reused with another nebulizer.

One embodiment of the present invention provides a method of treating a patient that exhibits one or more symptoms of infection or other respiratory disease or disorder. The method generally comprises the steps of: providing a vibration system comprising a circular vibratable aperture plate having an outer circumference, a tubular member concentrically disposed about the outer circumference of the vibratable plate, wherein the tubular member has an outer circumference, and an annular vibration-inducing member concentrically disposed about the outer circumference of the tubular member, wherein the vibration-inducing member is radially expandable and contractable to cause the aperture plate to vibrate in the axial direction; supplying a liquid medicament to the vibration system; actuating the vibration-inducing member to vibrate the aperture plate and aerosolize the medicament; and supplying the aerosol to the patient's respiratory system.

An aerosol generator in accordance with the present invention has the ability to produce a high flow of aerosol relative to the power input. For example, when standard saline solution (2% NaCl) is used, the flow rate of aerosol having a volumetric median diameter (VMD) of 4 microns may be 15 microliters/sec and the power consumption of the generator may be 3 watts.

The invention has now been described in detail for purposes of clarity and understanding. However, it will be appreciated that certain changes and modifications may be practiced within the scope of the appended claims.

What is claimed is:

1. An aerosol generator comprising:
an upper housing member having an upstream reservoir portion configured to receive liquid for aersolization;
a lower housing member forming a downstream portion of the aerosol generator;
a vibration system including:
a vibratable member including a center portion having a plurality of apertures therein and an annular flange surrounding the center portion;
a support member including a central hole and an annular mounting portion for receiving the annular flange of the vibratable member;
a ring-shaped piezoelectric member, wherein the vibratable member, support member, and piezoelectric member are separate elements bonded together and secured between the upper housing and the lower housing members;
a pair of electric lines in electrical communication with the piezoelectric member;
an upper ring-shaped seal on an upstream side of the vibration system; and
a lower ring-shaped seal on a downstream side of the vibration system;
wherein the piezoelectric member is configured to vibrate the vibratable member in response to the pair of electric lines transmitting an electric current to the piezoelectric member; and
wherein the upper and lower ring-shaped seals are configured to seal the piezoelectric member from liquid in the reservoir.

2. The aerosol generator of claim 1, wherein the ring-shaped piezoelectric member has an outer diameter that is larger than an opening in an upstream end of the lower housing member.

3. The aerosol generator of claim 2, wherein the central hole of the support member and a central opening in the piezoelectric member share a common central axis, and the central opening is larger than the central hole.

4. The aerosol generator of claim 3, wherein the center portion of the vibratable member extends in a downstream direction with respect to the annular flange.

5. The aerosol generator of claim 4, wherein the upper housing member and the lower housing member overlap one another when secured together.

6. The aerosol generator of claim 5, wherein the plurality of apertures of the vibratable member are tapered.

7. The aerosol generator of claim 6, wherein the support member is metal.

8. The aerosol generator of claim 7, wherein the vibratable member is configured to aerosolize the liquid in response to oscillation of the vibratable member.

9. The aerosol generator of claim 8, wherein the vibratable member is configured to eject the liquid as aerosol droplets via the plurality of apertures.

10. The aerosol generator of claim 9, wherein the upper housing is detachably engaged with the piezoelectric member.

11. An aerosol generator comprising:
a plate including a dome-shaped center portion with one or more apertures and an outer portion surrounded by a support structure engaging the outer portion of the plate to suspend the dome-shaped center portion concentric with the support structure;
a ring-shaped piezoelectric member in physical communication with the plate and configured to oscillate the plate;
a pair of electric lines in electrical communication with the ring-shaped piezoelectric member;
an upper housing forming a fluid reservoir for holding a fluid in fluid communication with the one or more apertures of the plate;
a lower housing member forming a downstream portion of the aerosol generator, wherein the ring-shaped piezoelectric member has an outer diameter that is larger than an opening in an upstream end of the lower housing member; and
a gasket forming a seal preventing the fluid from contacting the piezoelectric member, wherein the ring-shaped piezoelectric member is configured to oscillate the dome-shaped center portion in response to the pair of electric lines transmitting an electric current to the ring-shaped piezoelectric member;
wherein the plate and the support structure are disposed downstream of the fluid reservoir.

12. The aerosol generator of claim 11, wherein the plate is configured to receive the fluid along the dome-shaped center portion of the plate such that the medicament is disposed over the one or more apertures.

13. The aerosol generator of claim 12, wherein the plate is configured to aerosolize the fluid in response to the ring-shaped piezoelectric member oscillating the dome-shaped center portion.

14. The aerosol generator of claim 13, wherein the plate is configured to eject the fluid through the dome-shaped center portion as aerosol droplets via the one or more apertures.

15. The aerosol generator of claim 14, wherein the gasket comprises an elastomer seal or O-ring.

16. The aerosol generator of claim 15, wherein the plate and the support structure are surrounded by a wall that extends from the upper housing to a position below the plate and the support structure with respect to the upper housing.

17. An aerosol generator comprising:

a vibratable plate including a center portion and an outer supporting portion for supporting the center portion disposed about the center portion, the center portion having a plurality of apertures, a piezoelectric member in physical communication with the vibratable plate through the outer supporting portion;

a pair of electric lines in electrical communication with the piezoelectric member;

an upper housing and a lower housing, the upper housing and the lower housing forming a fluid reservoir and a fluid outlet with respect to the apertures, such that a fluid can flow through the apertures to the fluid outlet from the fluid reservoir;

a first gasket between the upper housing and the vibratable plate; and a second gasket between the lower housing and the vibratable plate the second gasket located downstream of the first gasket, wherein the piezoelectric member is configured to move the supporting portion to thereby oscillate the vibratable plate in response to the pair of electric lines transmitting an electric current to the piezoelectric member, such that the fluid received along the vibratable plate from the fluid reservoir is ejected as aerosolized droplets via the plurality of apertures to the fluid outlet in response to the vibratable plate oscillating, and wherein the piezoelectric member is isolated from contact with liquids.

18. The aerosol generator of claim 17, wherein the first gasket or the second gasket is an elastomer seal.

19. The aerosol generator of claim 17, wherein the first gasket is disposed on an upstream side of the vibratable plate and the second gasket is disposed on a downstream side of the vibratable plate.

* * * * *